United States Patent [19]

Anton et al.

[11] Patent Number: 5,219,745
[45] Date of Patent: Jun. 15, 1993

[54] PRODUCTION OF GLYOXYLIC ACID FROM GLYCOLIC ACID

[75] Inventors: David L. Anton; Robert DiCosimo; Lawrence W. Gosser, all of Wilmington, Del.

[73] Assignee: E. I. Du Pont de Nemours and Company, Wilmington, Del.

[21] Appl. No.: 705,419

[22] Filed: May 24, 1991

Related U.S. Application Data

[63] Continuation of Ser. No. 422,011, Oct. 16, 1989, abandoned.

[51] Int. Cl.$^5$ .......................... C12P 7/40; C12P 7/54; C12N 9/04
[52] U.S. Cl. .................... 435/136; 435/140; 435/190
[58] Field of Search ............... 435/190, 140, 136

[56] References Cited

U.S. PATENT DOCUMENTS

| | | | |
|---|---|---|---|
| 3,281,460 | 10/1966 | Gandon | 260/530 |
| 4,146,731 | 3/1979 | Ogahara et al. | 562/531 |
| 4,235,684 | 11/1980 | Harada et al. | 204/79 |
| 4,871,669 | 10/1989 | Murray et al. | 435/147 |

OTHER PUBLICATIONS

Tolbert et al., J. Biol. Chem., vol. 181, 905–914 (1949).
Zelitch et al., J. Biol. Chem., vol. 201, 707–718 (1953).
Robinson et al., J. Biol. Chem., vol. 237, 2001–2009 (1962).
Richardson et al., J. Biol. Chem., vol. 236, 1280–1284 (1961).
Clagett et al., J. Biol. Chem., vol. 178, 977–987 (1949).
Ullmanns Encyklopadie der Tecnischen Chemie, 4th Ed., vol. 12, Verlag Chemie, Weinheim, 1976, p. 381.

*Primary Examiner*—David M. Naff
*Assistant Examiner*—Mike Meller
*Attorney, Agent, or Firm*—Robert B. Stevenson

[57] ABSTRACT

A process for the production of glyoxylic acid involving the enzymatic oxidation of glycolic acid. The process provides a commercially practical method involving the reaction of glycolic acid in an aqueous solution at a starting concentration range of 200 mM to 2,500 mM in the presence of oxygen, glycolate oxidase and catalase at a pH of 7 to 10 and in the presence of an amine such as ethylenediamine, or tris(hydroxymethyl)-methylamine.

22 Claims, No Drawings

PRODUCTION OF GLYOXYLIC ACID FROM GLYCOLIC ACID

This is a continuation of application Ser. No. 07/422,011, filed Oct. 16, 1989, now abandoned.

BACKGROUND OF THE INVENTION

1. Field of the Invention

This invention concerns an improved process for the production of glyoxylic acid by the glycolate oxidase catalyzed oxidation of glycolic acid. Although the enzyme catalyzed reaction of glycolic acid with oxygen has been known for many years, the previously described processes have not proved commercially advantageous for several reasons. The most important of these is that previous reactions have been carried out at high dilutions of glycolic acid, typically concentrations of 40 mM or less. Selectivity for glyoxylic acid and yields of the glyoxylic acid product have usually been low. A disadvantage of the use of very dilute starting glycolic acid concentrations is the necessity for large and expensive reaction vessels to achieve high production rates. Also, since glyoxylic acid is usually sold as a 50% aqueous solution (Ullmans), concentrating the dilute glyoxylic acid produced using dilute starting reagents is costly. Further, if such concentration were done by evaporation or by reverse osmosis, any nonvolatile by-products such as oxalic and formic acids and/or their salts and unreacted glycolic acid would remain in solution as impurities. Finally, it would be advantageous if the relatively expensive enzymes used in the reaction could be used more efficiently or effectively recycled and if no environmentally detrimental wastes were produced.

The present invention provides a commercially practical method for the production of glyoxylic acid by the glycolate oxidase catalyzed oxidation of glycolic acid through the increase of starting substrate concentrations and through the use of selected yield improving additives.

2. Background Art

The present invention is a process for the production of glyoxylic acid by the oxidation of glycolic acid by oxygen, using an enzyme, glycolate oxidase, as a catalyst for the reaction.

N. E. Tolbert et al., *J. Biol. Chem.*, Vol. 181, 905-914 (1949) reported that an enzyme extracted from tobacco leaves catalyzed the oxidation of glycolic acid to formic acid and $CO_2$ via the intermediate glyoxylic acid. They further found that certain compounds such as ethylenediamine blocked the oxidation of the intermediate glyoxylic acid to other products. The oxidations were carried out at a pH of about 8, using glycolic acid concentrations of about 3-40 mM (millimolar), except for one experiment (p. 907), very poorly described, where the initial concentration of glycolic acid was somewhere between 132 and 196 mM. The only details given about this experiment are the approximate glycolic acid concentration, the fact that the oxidation was not run to completion, and that some amount of the 2,4-dinitrophenylhydrazone of glyoxylic acid was isolated. In particular, no details are given as to yields and the duration of the reaction. The optimum pH for the glycolate oxidation was reported to be 8.9. Oxalic acid (100 mM) was reported to inhibit the catalytic action of the glycolate oxidase.

I. Zelitch and S. Ochoa, *J. Biol. Chem.*, Vol. 201, 707-718 (1953) reported that the formation of formic acid and $CO_2$ in the glycolate oxidase catalyzed oxidation of glycolic acid resulted from the nonenzymatic reaction of $H_2O_2$ with glyoxylic acid, these being the primary products of the enzyme catalyzed oxidation of glycolic acid. Thus, they observed that addition of catalase, an enzyme that catalyzes the decomposition of $H_2O_2$, greatly improved the yields of glyoxylic acid by suppressing the formation of formic acid and $CO_2$. The glycolate oxidase they used was isolated from spinach leaves It was used at a pH of about 8, with an initial glycolic acid concentration of 10 mM. They also found that addition of FMN (flavin mononucleotide) greatly increased the efficiency of the glycolate oxidase.

J. C. Robinson et al., *J. Biol. Chem.*, Vol. 237, 2001-2009 (1962) also found that catalase increases the yield of glyoxylic acid from glycolic acid. They apparently used a ratio of about 80:1 of catalase:glycolate oxidase. They also concluded that the catalase was decomposing hydrogen peroxide produced in the glycolate oxidase catalyzed reaction of glycolic acid with oxygen (in their paper, glycolate oxidase is referred to as "short chain L-alpha-hdyroxy acid oxidase"). They found that FMN was helpful in maintaining glycolate oxidase activity. They also determined that the maximum rate of oxidation of glycolic acid catalyzed by glycolate oxidase occurs at a concentration of glycolic acid (substrate) of 3.3 mM and that, "The reaction was found to be inhibited, by: . . . (e) high concentrations of these substrates, glycolate, and . . .".

K. E. Richardson and N. E. Tolbert, *J. Biol. Chem.*, Vol. 236, 1280-1284 (1961) showed that buffers containing tris(hydroxymethyl)aminomethane inhibited the formation of oxalic acid in the glycolate oxidase catalyzed oxidation of glycolic acid. They too ran their reaction at a pH of about 8 and found that FMN increased glycolate oxidase efficiency. The maximum glycolic acid concentration they used was 20 mM.

C. O. Clagett, N. E. Tolbert and R. H. Burris, *J. Biol. Chem.*, Vol. 178, 977-987 (1949) discovered that the optimum pH for the glycolate oxidase catalyzed oxidation of glycolic acid with oxygen was about 7.8-8.6, and the optimum temperature was 35°-40° C. Their maximum substrate (glycolic acid) concentration was about 20 mM.

There are numerous other references to the oxidation of glycolic acid catalyzed by glycolic acid oxidase, for example:

Isolation of the enzyme (usually includes an assay method):

I. Zelitch in *Methods of Enzymology*, Vol. 1, Academic Press, New York, 1955, p. 528-532, from spinach and tobacco leaves.

M. Nishimura et al., *Arch. Biochem. Biophys.*, Vol. 222, 397-402 (1983), from pumpkin cotyledons.

H. Asker and D. Davies, *Biochim. Biophys. Acta*, Vol. 761, 103-108 (1983), from rat liver.

M. J. Emes and K. H. Erismann, *Int. J. Biochem.*, Vol. 16, 1373-1378 (1984), from Lemna Minor L.

Structure of the enzyme:

E. Cederlund et al., *Eur. J. Biochem.*, Vol. 173, 523-530 (1988).

Y. Lindquist and C. Branden, *J. Biol. Chem.*, Vol. 264, 3624-3628 (1989).

In all of the above references, and all others that have been studied [with the one exception noted above in the discussion of N. E. Tolbert et al., *J. Biol. Chem.*, Vol.

181, 905-914 (1949)], the maximum initial concentration of glycolic acid that has been used is about 40 mM, the pH has usually been about 8-9, FMN is sometimes added, an amine is sometimes added, and catalase is sometimes added. Other additives to improve the yield of glyoxylic acid have also been mentioned.

Numerous ordinary chemical (nonenzymatic) methods for the industrial synthesis of glyoxylic acid have been proposed, see for example U.S. Pat. Nos. 3,281,460, 4,146,731 and 4,235,684, as well as Ullmanns Encyklopadie der technischen Chemie, 4th Ed., Vol. 12, Verlag Chemie, Weinheim, 1976, p. 381 (herein Ullmanns). Some of these processes produce environmentally injurious products. None of these contemplate the oxidation of glycolic acid to glyoxylic acid.

Even though glycolic acid is an article of commerce, to Applicant's knowledge no one has previously contemplated using the glycolate oxidase catalyzed oxidation of glycolic acid for the production of glyoxylic acid. It is speculated that this may be due to the unfamiliarity of chemists and chemical engineers with enzyme reactions (biochemistry), the lack of recognition by biochemists that such a process was desirable, the relatively low yields or conversions reported in most of the literature, reported substrate inhibition and/or the low concentrations of substrate previously used.

SUMMARY OF THE INVENTION

This invention relates to a process for the production of glyoxylic acid comprising contacting, in an aqueous solution at a pH of about 7 to about 10, glycolic acid, glycolate oxidase and oxygen ($O_2$), in the presence of an effective amount of an additive that improves the yield of glyoxylic acid, wherein the initial glycolic acid concentration is 200 to about 2500 mM. The process is a practical one for commercial production in that it is characterized as being carried out at relatively high glycolic acid concentrations. Under optimum conditions, it also gives very high yields of glyoxylic acid at high conversion, and makes efficient use of the relatively costly enzyme(s) used in the process.

Glycolic acid concentrations of 200 to about 2500 mM may be used, and in addition to the glycolate oxidase catalyst, one or more compounds such as catalase and certain amines are also present to improve yields of glyoxylic acid. Added FMN is optionally present to improve the enzyme productivity. Oxygen, usually from the air or in a purer form (such as an industrial grade of oxygen) is used as the oxidant in the reaction. The reaction may be done at oxygen pressures above atmospheric pressure to increase the reaction rate.

DESCRIPTION OF THE INVENTION

This invention concerns the glycolate oxidase catalyzed oxidation of glycolic acid.

It has been determined that at initial substrate concentrations as high as about 2500 mM high yields of glyoxylic acid can be obtained. Yield can be further maximized by the addition of catalase or other additives alone or in combination. The high yield is unexpected in view of the reported substrate inhibition and/or possible product inhibition of the glycolate oxidase, and also the possible inhibition of the catalase, when present (for a discussion of substrate and product inhibition, see M. Dixon et al., Enzymes, 3rd Ed., Academic Press, New York, 1979, p. 96-7, 126-7, and T. Godfrey and J. Reichelt, Industrial Enzymology, The Nature Press, New York, 1983, p. 847). Indeed, we have found that at initial concentrations of glycolic acid over about 2500 mM the glycolate oxidase catalyzed reaction is relatively slow. This slowing of the rate of reaction becomes noticeable at initial concentrations over 1500 mM, and gradually gets worse as the substrate concentration increases. Fortunately, this slowing occurs at a high enough concentration so that a practical process can be operated. It has not been proven whether this slowing of the reaction rate is due to substrate or product inhibition or some other factor. Also the high concentrations of a selected additive (when present), such as an amine added to increase yield, could also cause inhibition or even denaturation of one or both enzymes.

Although high concentration of the substrate is the key to the commercially useful process described herein, other factors which enhance the usefullness of the process are the high selectivity to the glyoxylic acid product and the high conversion of the substrate to the glyoxylic acid product. In order to achieve a high yield of glyoxylic acid with very little by-product or side reaction, it has been found advantageous to add to the reaction mixture additives that improve the yield of glyoxylic acid, either the enzyme catalase, or a selected amine, such as ethylenediamine. The best yields are obtained when both catalase and a selected amine are added to the reaction. In addition, in order to increase the productivity of the glycolate oxidase, flavin mononucleotide (hereinafter FMN) may optionally be added in small amounts.

By the term "yield" herein is meant the percentage of glyoxylic acid obtained, based on the total amount of glycolic acid present at the beginning of the reaction. By the term "conversion" herein is meant the percentage of glycolic acid present at the beginning of the reaction that has reacted to form any other product. By the term "selectivity" herein is meant the percentage of glyoxylic acid obtained from the glycolic acid that has reacted. It therefore follows that, mathematically, yield equals conversion times selectivity. By the term "enzyme productivity" is meant the amount of glyoxylic acid produced per unit of enzyme.

Glycolic acid (2-hydroxyacetic acid) is available commercially from E. I. du Pont de Nemours and Company, Inc. In the present reaction its initial concentration is in the range cf 200 to about 500 mM, preferably about 250 to about 1500 mM and most preferably about 500 to about 1000 mM. Because the glycolate oxidase catalyzed oxidation is run at a pH of 7-10, during the oxidation it is believed glycolic acid is present as glycolate anion. It is to be understood herein that the use of the term glycolic acid, when referring to glycolic acid in a medium of pH higher than about 4, refers to glycolate anion.

The enzyme glycolate oxidase may be isolated from numerous sources (supra). According to the book Enzyme Nomenclature 1984, (Recommendations of the Nomenclature Committee if the International Union of Biochemistry on the Nomenclature and Classification of Enzyme-Catalyzed Reactions), Academic Press, New York, 1984 (hereinafter IUB), pg. 52-3, the systematic name for this type of enzyme is (S)-2-hydroxyacid oxidase and its Number is E.C. 1.1.3.15. IUB is hereby included by reference. The glycolate oxidase used in the reaction should be present in an effective concentration, usually a concentration of about 0.001 to about 1000 IU/mL, preferably about 0.1 to about 4 IU/mL. An IU (International Unit) is defined as the amount of enzyme that will catalyze the transformation of one micromole of substrate per minute. A procedure for the assay of this enzyme is found in I. Zelitch and S. Ochoa, J. Biol. Chem., Vol. 201, 707-718 (1953), which is hereby included by reference. This method is also used to assay the activity of recovered or recycled glycolate oxidase.

The pH of the reaction solution should be about 7 to about 10, preferably about 8.0 to about 9.5 and most preferably 8.0 to 9.0. The pH can be maintained by a buffer, since enzyme activity varies with pH. It has also been found that the pH of the reaction decreases slightly as the reaction proceeds, so it is often useful to start the reaction near the high end of the maximum enzyme activity pH range, about 9.0-9.5, and allow it to drop during the reaction. It has also been found that certain amines, such as ethylenediamine and tris(hydroxymethyl)methylamine (hereinafter TRIS) or mixtures thereof improve the yield of glyoxylic acid. Although inorganic buffers may be used, it is preferred to use excesses (over the molar amount of glycolic acid) of these amines to act as buffers, as well as improve yields. Ethylenediamine is preferred. Thus, these amines are used in a molar ratio of amine/glycolic acid (starting amount) of about 1.0 to about 3.0, preferably about 1.0 to 2.0, and most preferably about 1.05 to about 1.33. Within this range, the exact value may be adjusted to obtain the desired pH. With very basic amines used at high amine to glycolic acid ratios, it may be necessary to adjust the pH, as by adding acid, for example hydrochloric or sulfuric acids. With less basic amines such as TRIS, it may be necessary to add a base to maintain the desired pH. Although it is possible to use higher amounts of amines, such larger amounts usually have little or no beneficial effect and incur a cost penalty, especially in the isolation of the product. Thus, the lowest ratio of amine to glycolic acid consistent with obtaining the desired yield, selectivity and pH should preferably be used.

Another additive that may be used to increase the yield of glyoxylic acid is the enzyme catalase. Catalase [this is the systematic name, Number E.C. 1.11.1.6 (IUB)] catalyzes the decomposition of hydrogen peroxide to water and oxygen, and it is believed to improve yields in the present process by accelerating the decomposition of hydrogen peroxide which is a primary product in the glycolate oxidase catalyzed reaction of glycolic acid and oxygen to form glyoxylic acid. The concentration of catalase should be about 50 to about 100,000 IU/mL, preferably about 350 to about 14,000 IU/mL. It is preferred that the catalase and glycolate oxidase concentrations be adjusted within the above ranges so that the ratio (measured in IU for each) of catalase:glycolate oxidase is at least about 250:1.

FMN is an optional added ingredient, used at a concentration of 0.0 to about 2.0 mM, preferably about 0.01 to about 0.2 mM. It is believed the FMN increases the productivity of the glycolate oxidase. By productivity of the glycolate oxidase is meant the amount of glycolic acid converted to glyoxylic acid per unit of enzyme. It is to be understood that the concentration of added FMN is in addition to any FMN present with the enzyme, because FMN is often also added to the enzyme during the preparation of the enzyme. The structure of FMN and a method for its analysis is found in K. Yagai, *Methods of Biochemistry Analysis*, Vol. X, Interscience Publishers, New York, 1962, p. 319-355, which is hereby included by reference.

Oxygen ($O_2$) is the oxidant for the conversion of the glycolic acid to glyoxylic acid. For example, it may be added as a gas to the reaction by agitation of the liquid at the gas-liquid interface or through a membrane permeable to oxygen. Although not wanting to be bound by this hypothesis, it is believed that under most conditions, the reaction rate is at least partially controlled by the rate at which oxygen can be dissolved into the aqueous medium. Thus, although oxygen can be added to the reaction as the oxygen in air, it is preferred to use a relatively pure form of oxygen, and even use elevated pressures. Although no upper limit of oxygen pressure is known, oxygen pressures up to about 50 atmospheres are preferred, and up to about 15 atmospheres are most preferred. Agitation is important to maintaining a high oxygen dissolution (and hence reaction) rate. Any convenient form of agitation is useful, such as stirring. As is well known to those skilled in the art, high shear agitation or agitation that produces foam may decrease the activity of the enzyme(s), and hence should be avoided.

The reaction temperature is an important variable, in that it affects reaction rate and the stability of the enzymes. A reaction temperature range of about 0° to about 40° C. may be used, preferably a range of about 5° to about 30° C. and most preferably a range of 5° to 20° C. Of course, the temperature should not be so low that the water starts to freeze. These preferred temperatures are lower than those reported previously, and take into consideration preservation of enzyme activity as well as reaction (glycolate oxidation) rate. Temperature can be controlled by ordinary methods, such as, but not limited to, by using a jacketed reaction vessel and passing liquid of the appropriate temperature through the jacket.

The reaction vessel may be constructed of any material that is inert to the reaction ingredients.

Upon completion of the reaction, the enzymes may be removed by filtration, or if present in small enough amounts so that their presence is not injurious, be denatured by heating to 70° C. for 5 minutes. The amines are most conveniently removed by use of an ion exchange resin. An acidic cationic exchange resin is used to remove the amine. Suitable resins include Amberlite CG120, Amberlite IR120 (made by Rohm & Haas Co.) and Dowex 50 (made by Dow Chemical Co.). The amine may then be recovered and subsequently recycled by treatment of the resin with strong base. Filtration of the enzymes and amine recovery are further illustrated by the Examples.

The product glyoxylic acid is useful in the preparation of vanillin, ethylvanillin, as well as being used in ion exchange resins and as an acid catalyst in the pharmaceutical industry (Ullmanns). As mentioned above, it is usually sold as a 50% weight percent aqueous solution. It is also to be understood that reference to glyoxylic acid in this Application can also mean the glyoxylate anion, especially when the glyoxylic acid is present in a solution whose pH is greater than about 2.3.

In the following Examples and Experiments, stirring was done with a magnetic stirrer bar except where otherwise indicated. Remaining enzyme activity was measured by withdrawing an aliquot from the reaction and assaying directly using standard assay techniques (supra).

It is crucial in these Examples and Experiments to have an accurate analytical method. It has been found that high performance liquid chromatography (HPLC) is an excellent analytical method, and it was used for the analyses reported herein.

HPLC Method

Samples for analysis were prepared by mixing 100 μL of the reaction mixture with 300 μL of 0.1 N $H_2SO_4$, then filtering the resulting solution through a Millipore Ultrafree MC filter unit (10,000 mw cutoff). Analyses for glycolic acid, glyoxylic acid, oxalic acid and formic acid were performed by HPLC on a Bio-Rad Aminex HPX-87H column (300×7.8 mm) at 40° C., using as solvent an aqueous solution of $H_2SO_4$ (0.01 N) and 1-hydroxyethane-1,1-diphosphonic acid (0.1 mM) at 1.0 mL/minute. The instrument was a Waters 840 HPLC system with Model 510 pumps, a 712 WISP autosampler, and, in sequence, a 490E UV detector and 410 differential refractometer. UV analysis was performed at 210 nm. The retention times for oxalic acid, glyoxylic acid, glycolic acid, formic acid, and propionic acid (internal standard) were 4.29, 6.09, 7.77, 8.79, and 11.41 minutes, respectively.

EXPERIMENT 1

Spinach leaves (2000 g) were homogenized in a 4 L commercial blender containing 1000 mL of 0.1 M potassium phosphate buffer, pH 8.0 at 40° C. The pulp was squeezed through 4 layers of cheesecloth, yielding 1800 mL of juice. The extract was acidified to pH 5.2 by the addition of approximately 1 mL of glacial acetic acid. The mixture was centrifuged at 14000 x g for 15 minutes to remove solids. To the supernatant was added solid ammonium sulfate (10.6 g/100 mL of extract) in order to achieve 20% the addition of 6 N KOH. After the solution was allowed to stand for 15 minutes, it was centrifuged for 20 minutes at 14000× g and the pellet was discarded. Ammonium sulfate (8.3 g/100 mL) was added to the supernatant for a total of 35% saturation. The precipitate was collected after 15 minutes by centrifugation at 14000 x g for 20 minutes. The pellet was dissolved in a minimal volume (ca. 180 mL) of 20 mM ethylenediamine-HCL, pH 8.0 containing 2 mM flavin mononucleotide. Once dissolved, ammonium sulfate was added to a final concentration of 3.2 M. The glycolate oxidase-ammonium sulfate suspension was stored in darkness at 4° C.

EXAMPLE 1

Oxidation of Glycolic Acid

Into a 3 ounce Fischer-Porter glass aerosol reaction vessel were placed a magnetic stirring bar and 10 mL of an aqueous solution containing glycolic acid (250 mM), ethylenediamine (EDA) (330 mM), FMN (0.01 mM), propionic acid (HPLC internal standard, 75 mM), glycolate oxidase (GAO) (from spinach; 2.0 IU/mL), and catalase (from *Aspergillus niger*; 1400 IU/mL). The final pH of this solution was 8.9. The reaction vessel was sealed and the reaction mixture was cooled to 15° C., then the vessel was flushed with oxygen by pressurizing to 70 psig and venting to atmospheric pressure five times with stirring. The vessel was then pressurized to 70 psi of oxygen and the mixture stirred. Aliquots (0.10 mL) were removed through a sampling port (without loss of pressure in the vessel) at regular intervals for analysis by HPLC to monitor the progress of the reaction. After 4 hours, the HPLC yields of glyoxylate, oxalate, and formate were 98.9%, 0.5%, and 0%, respectively, and 0.6% glycolate remained. The remaining activity of glycolate oxidase and catalase were both 100% of their initial values.

EXAMPLE 2

Oxidation of Glycolic Acid

The reaction of Example 1 was repeated, except that $K_2HPO_4$ (330 mM) was substituted for ethylenediamine and the final pH of the solution was adjusted to pH 8.0 with concentrated HCl. After 4 hours, the HPLC yields of glyoxylate, oxalate, and formate were 24.4%, 0.3%, and 8.4%, respectively, and 67.1% glycolate remained. The remaining activity of glycolate oxidase and catalase were 95% and 44% of their initial values, respectively.

EXAMPLE 3

Oxidation of Glycolic Acid

Into a 3 ounce Fischer-Porter glass aerosol reaction vessel were placed a magnetic stirring bar and 50 mL of an aqueous solution containing glycolic acid (750 mM), ethylenediamine (862 mM), FMN (0.1 mM), propionic acid (HPLC internal standard, 75 mM), glycolate oxidase (from spinach; 1.0 IU/mL), and catalase (from *Aspergillus niger*; 1400 IU/mL). The final pH of this solution was 8.9. The reaction vessel was sealed and the reaction mixture was cooled to 15° C., then the vessel was flushed with oxygen by pressurizing to 70 psig and venting to atmospheric pressure five times with stirring. The vessel was then pressurized to 70 psi of oxygen and the mixture stirred, and 0.10 mL aliquots were removed at regular intervals for analysis by HPLC to monitor the progress of the reaction. After 90 hours, the HPLC yields of glyoxylate, oxalate, and formate were 99.8%, 0.2%, and 0%, respectively, and no glycolate remained. The remaining activity of glycolate oxidase and catalase were 34% and 88% of their initial values, respectively.

EXAMPLE 4

Oxidation of Glycolic Acid

Into a 3 ounce Fischer-Porter glass aerosol reaction vessel were placed a magnetic stirring bar and 10 mL of an aqueous solution containing glycolic acid (2000 mM), ethylenediamine (2100 mM), FMN (0.01 mM), glycolate oxidase (from spinach; 1.2 IU/mL), and catalase (from *Aspergillus niger*; 1400 IU/mL). The final pH of this solution was 9.0. The reaction vessel was sealed and the reaction mixture was cooled to 15° C., then the vessel was flushed with oxygen by pressurizing to 70 psig and venting to atmospheric pressure five times with stirring. The vessel was then pressurized to 70 psi of oxygen and the mixture stirred, and 0.10 mL aliquots were removed at regular intervals for analysis by HPLC to monitor the progress of the reaction. After 31 hours, no glycolate oxidase activity remained, so an additional 2.0 IU/mL of glycolate oxidase was added. After 143 hours, the HPLC yields of glyoxylate, oxalate, and formate were 96.8%, 2.2%, and 1.0%, respectively, and no glycolate remained. The remaining activity of glycolate oxidase (based on total) and catalase were 69% and 100% of their initial values, respectively.

EXAMPLE 5

Oxidation of Glycolic Acid

Into a 3 ounce Fischer-Porter glass aerosol reaction vessel were placed a magnetic stirring bar and 10 mL of an aqueous solution containing glycolic acid (250 mM), tris(hydroxymethyl)aminomethane (TRIS, 330 mM), FMN (0.02 mM), propionic acid (HPLC internal standard, 75 mM), glycolate oxidase (from spinach; 0.25

IU/mL), and catalase (from *Aspergillus niger*; 1400 IU/mL). The final pH of this solution was adjusted to 8.3 with 5% NaOH. The reaction vessel was sealed and the reaction mixture was cooled to 30° C., then the vessel was flushed with oxygen by pressurizing to 15 psig and venting to atmospheric pressure five times with stirring. The vessel was then pressurized to 15 psi of oxygen with stirring. Aliquots (0.10 mL) were removed through a sampling port (without loss of pressure in the vessel) at regular intervals for analysis by HPLC to monitor the progress of the reaction. After 30 hours, the HPLC yields of glyoxylate, oxalate, and formate were 89.5%, 3.3%, and 2.8%, respectively, and no glycolate remained. The remaining activity of glycolate oxidase and catalase were 52% and 60% of their initial values, respectively.

EXAMPLE 6

Oxidation of Glycolic Acid

The reaction in Example 4 was repeated, except that the concentrations of glycolic acid and ethylenediamine were 2500 mM and 2630 mM, respectively, and no additional glycolate oxidase was added at 31 hours. After 143 hours, the HPLC yields of glyoxylate, oxalate, and formate were 27.4%, 0%, and 0%, respectively, and 72.6% glycolate remained, indicating a decrease in the rate of the reaction at 2500 mM glycolate. The remaining activity of glycolate oxidase and catalase were 68% and 80% of their initial values, respectively.

EXAMPLE 7

Effect of Temperature of Oxidation of Glycolic Acid

The dependence of catalase and GAO activity on the reaction temperature was determined using a 3 ounce Fischer-Porter glass aerosol reaction vessel. Aqueous solutions (10 mL) containing glycolate (250 mM), ethylenediamine (330 mM), glycolate oxidase (0.5 IU/mL), catalase (1400 IU/mL), and FMN (0.01 mM) were, stirred at various temperatures at pH 8.3 under 1 atmosphere of oxygen. After 1 hour, the yields of glyoxylate from reactions performed at 40° C., 30° C., 15° C., and 5° C. were 92%, 96%, 99%, and 99%, respectively, while the remaining catalase/GAO activity was 38%/87%, 60%/100%, 100%/100%, and 100%/100%, respectively. Lower reaction temperatures result in higher remaining enzyme activities at high glyoxylic acid selectivities.

EXAMPLE 8

Effect of Oxygen

Using the procedure described in Example 1, aqueous solutions (10 mL) containing glycolic acid (250 mM), TRIS buffer (330 mM, pH 8.3), propionic acid (HPLC internal standard, 75 mM), glycolate oxidase (spinach; 0.25 IU/mL), catalase (Aspergillus niger; 1400 IU/mL), and FMN (0.2 mM) were stirred at 30° C. under 1 atmosphere of air (0.2 atmosphere of oxygen) or 1, 2, 3, 6, or 10 atmospheres of oxygen. The initial rates of production of glyoxylic acid (over the first 10-15% of the reaction) at the various oxygen pressures employed are listed in the table below.

| Oxygen Pressure (atmospheres) | Rate (μmol/mL/minute |
| --- | --- |
| 0.2 | 0.027 |
| 1.0 | 0.156 |
| 2.0 | 0.301 |
| 3.0 | 0.494 |
| 6.0 | 0.752 |
| 10.0 | 1.025 |

EXAMPLE 9

Effect of Glycolate Oxidase

Using the procedure described in Example 1, aqueous solutions (10 mL) containing glycolate (250 mM), EDA (330 mM), propionic acid (HPLC internal standard, 75 mM), glycolate oxidase (0.20, 0.40, or 4.0 IU/mL), catalase (1400 IU/mL), and FMN (0.01 mM) were stirred at 15° C. and pH 8.9 under 6 atmospheres of oxygen. The initial rates of production of glyoxylic acid (over the first 10-15% of the reaction) when using 0.20 IU/mL, 0.40 IU/mL, or 4.0 IU/mL of beet GAO were 1.37 μmol)/mL/minute, 1.33 μmol)/mL/minute, and 1.32 μmol)/mL/minute, respectively. Under these general reaction conditions, there was no dependence of the reaction rate on enzyme concentration.

EXAMPLE 10

Oxidation of Glycolic Acid

Demonstration of the enzymatic synthesis of glyoxylic acid on a large scale was performed in an Amicon Model 2000 High-Output Stirred Cell, where a 1.6 mm thick Teflon ® sheet was substituted for the filtration membrane, and which had a magnetically driven paddle stirrer. Glycolate oxidase (2000 IU, isolated from spinach) was added to 2.0 L of solution containing glycolic acid (113 g, 1.49 moles), ethylenediamine (95 g, 1.58 moles), FMN (9.7 mg, 0.02 mmoles), and catalase [$2.8 \times 10^6$ IU, from *Aspergillus niger* (Sigma)], and the resulting mixture (final pH = 8.9) was stirred at 15° C. under 6 atmospheres of oxygen. Aliquots were removed at regular intervals for analysis by HPLC to monitor the progress of the reaction. After 77 hours, HPLC analysis of the reaction mixture indicated that glyoxylic acid (110 g, 99.6% yield), formic acid (0.2%), and oxalic acid (0.2% yield) were the only reaction products; complete conversion of glycolic acid was attained. Glycolate oxidase and catalase activities were 74% and 87% of their initial activities, respectively The reaction was terminated by sparging the solution with nitrogen, then heating the reaction mixture to 70° C. for 5 minutes under a nitrogen blanket. Precipitated protein was removed by centrifugation, and FMN removed by filtration of the reaction mixture through activated carbon. Any remaining soluble protein was removed by filtration using a Millipore Minitan Filtration System with a 10,000 mw cutoff filter, then glyoxylate and ethylenediamine (EDA) were separated by ion exchange chromatography.

Amberlite CG-120 (900 g, Rohm & Haas, 100-200 mesh, 4.5 meq/g) was suspended in 1.0 N HCL to yield 2.0 L of swollen resin, which was then rinsed with distilled water to remove excess HCL. A 50×100 cm Pharmacia K column was packed with 1900 ml of washed resin, 2.0 L of distilled water was pumped through the column at 8.0 mL/minute, then one-half of the glyoxylic acid/ethylenediamine (EDA) reaction mixture (containing 0.78 moles of EDA and 0.75 moles of glyoxylic acid) was loaded onto the column at a flow rate of 8 ml/minute. Glyoxylic acid was collected during an initial water elution phase, which was monitored by absorbance at 254 nm. Approximately 2.2 L of glyoxylic acid-containing eluent were collected. Ethylenediamine was eluted with 3.4 L of 1 N NaOH, yielding 0.77 moles of EDA (99% recovery). The column was reequilibrated by washing with 1 N HCl (2.4 L) followed by 3 L of distilled water to remove chloride. The combined column fractions containing glyoxylic acid from the ion exchange column separation of two 1.1 L fractions of the glyoxylic acid/EDA eluate were combined and concentrated by rotary evaporation at 40° C. to produce a 50 wt.% solution containing 1.40 moles (94% yield) of glyoxylic acid; the purity of the glyoxylic acid produced was greater than 99.5% as determined by $^{13}$C NMR spectroscopy and HPLC analysis.

EXAMPLE 11

Oxidation of Glycolic Acid

The reaction in Example 1 was repeated, except that the addition of catalase was omitted. After 4 hours, the HPLC yields of glyoxylate, oxalate, and formate were 6.2%, 0.7%, and 16.3% respectively, and 7.1% glycolate remained, demonstrating the lower selectivities obtained when catalase is absent. The remaining activity of glycolate oxidase was 5% of its initial value.

EXAMPLE 12

Oxidation of Glycolic Acid

A stock solution was prepared by mixing 12.5 g of deionized water, 300 mg of glycolic acid, 1.2 g of TRIS and 1.0 g of a 0.02 mM solution of FMN in a pH 6.8 phosphate buffer. A 10 g portion of the stock solution was placed in a 250 mL Erlenmeyer flask with 2 mg of bovine liver catalase (purchased from Sigma Chemical Co., St. Louis, MO, 63178, catalog number C-10, about 1200 IU/mg). A 0.5 g portion of a glycolate oxidase suspension (Sigma catalog number G-4136, from sugar beets, the solution containing 2.4 M $(NH_4)_2SO_4$, 10 mM TRIS, 5 mM FMN, and having about 7.5 IU/ml) was centrifuged and the liquid was discarded. The solid was added to the solution in the Erlenmeyer flask. The pH was 8.5. The flask was purged with oxygen for 5 min at about 200 mL $O_2$/min. The flask was sealed and then shaken with a wrist action shaker for about 23 hr. Analysis by HPLC (similar to but not exactly the same as described above) showed that the glycolate had been completely oxidized to glyoxylate and a small amount of oxalate.

EXAMPLE 13

Oxidation of Glycolic Acid Using a "Membrane Reactor"

A stock solution was prepared by mixing 12.4 mL of deionized water, 305 mg of glycolic acid, 1.0 g of 0.15 mM FMN in a pH 7.5 phosphate buffer, and 1.3 g of 20 weight percent solution of ethylenediamine in water. A reaction mixture was prepared by mixing 12 g of the stock solution, 4 mg of bovine liver catalase (Sigma, catalog number C-10, about 2800 IU/mg), and the centrifuged solid from 1.0 g of a commercial glycolate oxidase suspension (Sigma G-8620, containing 3.2 M $(NH_4)_2SO_4$, 2 mM FMN, 2.8 IU/mL, the glycolate oxidase being isolated from spinach). The pH was 9.1.

The reactor had 3 components, a 3.65 M length of 1.6 mm ID by 3.2 mm OD silicone rubber tubing (Dow Corning Corp.), a Masterflex peristaltic pump, and a 10 mm ID by 100 mm long (glass) test tube which served as a reservoir. The tubes to and from the pump passed through a septum which closed the test tube reservoir. The reaction mixture was put into the reactor and then pumped through the tubing for about 23 hr at a rate of 3.5 mL/min. During this time about 5 mL was in the tubing and 5 mL was in the reservoir (but all was circulated around). The tubing was coiled loosely in a gentle flow of air. HPLC analysis (similar to but not exactly the same as described above) showed complete oxidation of the glycolate to qlyoxylate and a small amount of oxalate.

EXPERIMENT 2

Oxidation of Glycolic Acid

Into a 15 mL polypropylene centrifuge tube were placed 3 mL of an aqueous solution containing glycolic acid (3.3 mM), $K_2HPO_4$ (33 mM, pH 8.0), glycolate oxidase (spinach, 0.33 IU/mL), catalase (bovine liver, 1400 IU/mL), and FMN (0.01 mM). The solution was maintained at 30° C. in air, and 0.15 mL aliquots were removed, filtered through a Millipore 10,000 MW cut-off filter, and analyzed by HPLC. After 1 hour, the yields of glyoxylate, oxalate, and formate were 80.9%, 3.8%, and 0%, respectively, and 15.5% glycolate remained After 2 hours, the yields of glyoxylate, oxalate, and formate were 80.6%, 19.7%, and 0%, respectively, and no glycolate remained.

Although preferred embodiments of the invention have been described hereinabove, it is to be understood that there is no intent to limit the invention to the precise constructions herein disclosed, and it is to be further understood that the right is reserved to all changes and modifications coming within the scope of the invention as defined by the appended claims.

What is claimed is:

1. A process for the production of glyoxylic acid, comprising contacting in aqueous solution, at a pH of about 7 to about 10, glycolic acid, glycolate oxidase and oxygen, in the presence of catalase, wherein the initial concentration of said glycolic acid is 200 mM to about 2,500 mM, and an amine, selected from the group consisting of ethylenediamine, tris(hydroxymethyl)methylamine, and mixtures thereof, is also present, and provided that the initial molar ratio of said amine to said glycolic acid is about 1.0 to about 3.0 and the concentration of said catalase is about 50 IU/mL to about 100,000 IU/mL and recovering said glyoxylic acid.

2. The process of claim 1 wherein the initial glycolic acid concentration is about 250 mM to about 1500 mM.

3. The process of claim 1 wherein the glycolate oxidase is present at a concentration of about 0.001 to about 1000 IU/mL.

4. The process of claim 1 wherein the pH is 8.0 to 9.5.

5. The process of claim 1 wherein the pH is adjusted to about 9.5 at the start of the reaction and is permitted to decrease to as low as about 8.0 as the reaction proceeds.

6. The process of claim 1 wherein the concentration of catalase is about 350 to about 14,000 IU/mL.

7. The process of claim 1 wherein the ratio of catalase to glycolate oxidase is at least 250:1.

8. The process of claim 1 wherein the temperature is about 0° C. to about 40° C., provided, however, that the temperature is not so low that water in the reaction mixture freezes.

9. The process of claim 1 wherein the oxygen is added as a gas at atmospheric pressure, up to a pressure of about 50 atmospheres.

10. The process of claim 1 wherein flavin mononucleotide is present in an initial concentration of about 2.0 mM or less.

11. The process of claim 1 wherein the oxygen for the reaction is added as a gas and is contacted with the aqueous solution by agitation of the solution at an interface between the oxygen and the reaction solution.

12. The process of claim 11 wherein the oxygen is added through a membrane permeable to oxygen.

13. The process of claim 1 wherein any enzymes present after the reaction are removed by filtration and/or heating.

14. The process of claim 1 wherein any amines present after the reaction are removed by use of an ion exchange resin.

15. The process of claim 1 wherein the amine is ethylenediamine.

16. The process of claim 1 wherein the amine is tris(hydroxymethyl)methylamine.

17. The process of claim 1 wherein the amine is a mixture of ethylenediamine and tris(hydroxymethyl)methylamine.

18. The process of claim 1 wherein the initial amine to glycolic acid ratio is about 1.0 to about 2.0 and the initial concentration of glycolate oxidase is about 0.001 to about 1000 IU/mL.

19. The process of claim 18 wherein the initial amine to glycolic acid ratio is about 1.05 to about 1.33, and the initial concentration of catalase is about 350 to about 14,000 IU/mL and the initial concentration of glycolate oxidase is about 0.1 to about 4.0 IU/mL.

20. The process of claim 19 wherein the pH is 8.0 to 9.5.

21. The process of claim 19 wherein the temperature is about 20° C. to about 40° C.

22. The process of claim 19 wherein the flavin mononucleotide is present in an initial concentration of 2.0 mM or less.

* * * * *